United States Patent
Hwang et al.

(10) Patent No.: US 8,802,167 B2
(45) Date of Patent: Aug. 12, 2014

(54) **USE OF *ECLIPTA PROSTRATA* AND OTHER PPAR-GAMMA INHIBITORS IN COSMETICS AND COMPOSITIONS THEREOF**

(75) Inventors: Cheng S. Hwang, New Milford, NY (US); Uma Santhanam, Tenafly, NJ (US); Manpreet Randhawa, Nanuet, NY (US)

(73) Assignee: Avon Products, Inc., New York, NY (US)

( * ) Notice: Subject to any disclaimer, the term of this patent is extended or adjusted under 35 U.S.C. 154(b) by 519 days.

(21) Appl. No.: 13/115,395

(22) Filed: May 25, 2011

(65) Prior Publication Data

US 2011/0305781 A1 Dec. 15, 2011

Related U.S. Application Data

(60) Provisional application No. 61/353,832, filed on Jun. 11, 2010.

(51) Int. Cl.
| | | |
|---|---|---|
| *A61K 36/28* | (2006.01) | |
| *A61K 36/00* | (2006.01) | |
| *A61K 8/97* | (2006.01) | |
| *A61Q 19/06* | (2006.01) | |

(52) U.S. Cl.
CPC . *A61Q 19/06* (2013.01); *A61K 8/97* (2013.01); *A61K 36/28* (2013.01)
USPC .......................................... 424/764; 424/725

(58) Field of Classification Search
None
See application file for complete search history.

(56) References Cited

U.S. PATENT DOCUMENTS

| | | | | |
|---|---|---|---|---|
| 5,962,482 | A * | 10/1999 | Bissett | 514/356 |
| 6,048,533 | A | 4/2000 | Nguyen | |
| 7,410,658 | B2 * | 8/2008 | Wang et al. | 424/725 |
| 2001/0041708 | A1 | 11/2001 | Halvorsen et al. | |
| 2005/0191267 | A1 | 9/2005 | Luanratana | |
| 2006/0018867 | A1 | 1/2006 | Kawaski et al. | |
| 2010/0015262 | A1 | 1/2010 | Goralczyk et al. | |

FOREIGN PATENT DOCUMENTS

| | | | |
|---|---|---|---|
| CN | 101244221 | A | 8/2008 |
| EP | 1736142 | A1 | 12/2006 |
| JP | 2000143437 | A | 5/2000 |
| KR | 2004016331 | A * | 2/2004 |
| KR | 776346 | B1 | 6/2006 |
| WO | 00/09754 | | 2/2000 |
| WO | 2004/047746 | A2 | 6/2004 |
| WO | 2009/019566 | A1 | 2/2009 |

OTHER PUBLICATIONS

Rhonda Allison (Red Indulgence—the Rhonda Allison Limited Edition Red Box) Sep. 2010.*
De Vries et al.; Adipose tissue fatty acid composition and its relations to diet and plasma lipid concentrations in hermodialysis patients; Am J. Clin Nutrition. 1991; 53:469-73.
Ntambi et al.; Loss of stearoyl—CoA desaturase-1 function protects mice against adiposity; PNAS 2002; 99:11482-11486.
Zweers et al.; Transplantation of reconstructed human skin on nude mice: a model system to study expression of human tenascin-X and elastic fiber components; Cell Tissue Res, 2005, 319:279.
Matsumoto et al.; Triglyceride accumulation and altered composition of triglyceride-associated fatty acids in the skin of tenascin-X-deficient mice; Genes to Cells, 2004, 9, 737-748.
Dixit, S P et al.; Study of Bhringaraja (*Eclipta alba*) Therapy in Jaundice in Children; Journal of Scientific Research in Plants and Medicines; 1981, vol. 2, No. 4, p. 96-100.
Kumar, "Reducing Cellulite on Things". Articlebase, Feb. 15, 2008, http://rajkumar.articlebase.com/health-articles/reducing-cellulite-on-thighs-334490.html.

* cited by examiner

*Primary Examiner* — Chris R Tate
*Assistant Examiner* — Deborah Davis
(74) *Attorney, Agent, or Firm* — David M. Loyal; Joan M. McGillycuddy

(57) ABSTRACT

The present invention describes compositions and methods for improving the appearance of skin, particularly, treating, ameliorating, preventing, delaying, and/or improving one or more signs of excess accumulation and/or production of subcutaneous fat, such as cellulite, and conditions related thereto, by topically applying compositions comprising *Eclipta prostrata* extracts or other anti-lipid agents.

21 Claims, No Drawings

USE OF ECLIPTA PROSTRATA AND OTHER PPAR-GAMMA INHIBITORS IN COSMETICS AND COMPOSITIONS THEREOF

RELATED APPLICATIONS

This application claims priority to U.S. Provisional Patent Application Ser. No. 61/353,832, filed Jun. 11, 2011, the contents of which are hereby incorporated by reference in their entirety.

FIELD OF THE INVENTION

The present invention relates generally to cosmetic compositions for topical application to the skin which comprise at least one anti-lipid agent and the use of such compositions to provide benefits to the skin, in particular, in improving the condition and appearance of skin affected by cellulite.

BACKGROUND OF THE INVENTION

Consumers continually seek to improve the appearance of their skin and in particular to reduce appearance of skin affected by unwanted deposition and/or accumulation of fat, including cellulite. There is active interest in the cosmetics industry to develop products that may be applied topically to the skin to provide anti-cellulite benefits, as well as other anti-lipid benefits. Cosmetic products that enhance the appearance of skin are increasingly in demand as consumers increasingly seek to mitigate and delay signs of excess accumulation and/or production of subcutaneous fat.

Peroxisome proliferator-activated receptor-gamma (PPAR-γ) is a member of the nuclear receptor family of transcription factors involved in the regulation of lipid biosynthesis. PPAR-γ heterodimerizes with retinoid X receptor (RXR), leading to transactivation of genes that encode proteins involved in adipogenesis. PPAR-γ agonists (e.g. rosiglitazone) have been shown to increase fat synthesis and storage in adipocytes; whereas lipid accumulation and adipocyte differentiation are impaired when PPAR-γ levels are reduced.

Stearoyl-CoA desaturase-1 (SCD1) is a key lipogenic enzyme that catalyzes the synthesis of monounsaturated fatty acids. Its preferred desaturation substrates are palmitoyl-CoA and stearoyl-CoA, which are converted to palmitoleoyl-CoA and oleoyl-CoA, respectively. Oleic acid constitutes nearly half of the total fatty acids in the adipose tissue (de Vries, Am J. Clin Nutrition. 1991; 53:469-73). The absence of SCD1 leads to reduced triglycerides synthesis, decreased lipid storage, and decreased lipid export. Further, SCD1-deficient mice have shown that loss of SCD1 increases the expression of genes involved in fatty acid oxidation and reduces the expression of lipogenic genes. As a result of changes in gene expression, SCD1-deficient mice have reduced body fat and increased energy expenditure and oxygen consumption (Ntambi et al. PNAS 2002; 99:1 1482-11486).

Tenascin X is a member of the Tenascin family of proteins, a family of large oligomeric glycoproteins found in the extracellular matrix. Tenascins are responsible for modulating cell-matrix interactions and influencing cell functions. Tenascin-X is expressed in connective tissues, such as skin, joints, and muscles, and plays a critical role in remodeling and maintaining the integrity of skin. Deficiency causes one of the types of Ehlers-Danlos syndrome, a heritable connective tissue disorder characterized by connective tissue defects, such as reduced collagen deposition, different mechanical properties of dense tissues, and fragmentation of elastic fibers in the skin. In vitro studies have demonstrated that tenascin-X deficient fibroblasts fail to deposit collagen type I in the matrix. Further, culture grafting experiments have demonstrated that the expression of tenascin-X is required for the organization of fibrillin I and elastin into a fibrillar network (Zweers et al, 2005, Cell Tissue Res, 319:279). Moreover, tenascin-X deficient mice have been shown to increase lipid accumulation in subcutaneous adipose tissue and reduce the density of collagen fibrils, which is similar to the characteristics of cellulite-affected skin (Ken-ichi Matsumoto et al. 2004, Genes to Cells, 9, 737-748).

Active ingredients derived from plants and plant seeds have commonly been employed for a myriad of medicinal, therapeutic and cosmetic purposes. Such actives may be obtained from the entire plant or various parts of a plant, such as seeds, needles, leaves, roots, bark, cones, stems, rhizomes, callus cells, protoplasts, organs, organ systems, and meristems. Active ingredients can be incorporated in compositions in a variety of forms. Such forms include a pure or semi-pure component, a solid or liquid extract or derivative, or a solid natural plant material. Plant material also may be incorporated in a variety of sub-forms such as whole, minced, ground or crushed. A common problem when using an active ingredient derived from a plant material and/or plant seed, however, is the relatively low level at which they naturally occur. Such low levels frequently require relatively large amounts of the natural plant material be processed in order to obtain desired or useful quantities of actives, and specific extraction procedures may be required.

*Eclipta prostrata* Linn., also known as *Eclipta alba* (L) Hassk, of the Family Astraceae, is a common plant found growing in moist soils throughout India and can reach a height of about 6,000 ft. *Eclipta prostrata* is used in traditional Indian medicines, e.g., as to treat cirrhosis of the liver and infective hepatitis (Dixit, S. P. et al. Journal of Scientific Research in Plants and Medicines 1981, 2, 96-100). In addition, the plant is used to treat hyperglycemia and hyperlipidemia by inhibiting, it is believed, gluconeogenesis and possibly also modulating lipid metabolism and excretion in the liver. A topical cosmetic composition having an active ingredient derived from a plant material, or extract thereof, would be desired in improving the appearance of skin in the treatment, control, management, amelioration, prevention, inhibition, delay, and/or reduction of excess accumulation and/or production of subcutaneous fat, including cellulite.

Cellulite is the lumpy uneven type of subcutaneous fat that tends to accumulate on the buttocks, thighs, and limbs of many women. It is considered unsightly because it gives the tissues underlying the skin an "orange peel" or "cottage cheese" look. Compressing the skin, as when sitting or crossing the legs, produces a "mattress appearance" with bulging and pitting of the fatty layer. Nodules of fat may be felt trapped within hardened connective tissue. The histology of cellulite-affected skin indicates that cellulite results from a combination of enlarged fat tissue and weak dermal structure and connective tissue septa. Excess fat accumulation increases the volume of adipocytes, which bulge into a weakened dermis to create the characteristic irregularities in the appearance of the epidermal surface. A number of factors can cause cellulite including, e.g., hereditary, intestinal, circulatory, lymphatic, hormonal, and lifestyle factors. Dieting to decrease fat intake, exercise to increase fat metabolism and prevent the build up of cellulite, and massage and hydrotherapy to stimulate lymphatic drainage can help reduce the appearance of cellulite. Nonetheless, these means for combating cellulite or subcutaneous fat are limited, and the need remains for additional approaches.

Therefore, safe, effective, natural, and new ingredients to treat, ameliorate, prevent: inhibit, delay, and/or reduce the signs of excess accumulation and/or production of subcutaneous fat, and/or improve dermal architecture by strengthening connective tissue, would be advantageous for topical compositions useful as skin products. Novel methods and compositions, as well as their mode of action, are provided herein for treating conditions related to excess accumulation and/or production of subcutaneous fat, including cellulite, as well as skin formulations comprising same, and other personal care products for the skin.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

It has surprisingly been found that compositions comprising one or more substances that inhibit PPARγ, and additionally also inhibit stearoyl-CoA desaturase 1 (SCD1) and/or also stimulate tenascin-X production, show superior improvement in the appearance of skin affected by unwanted fat deposition and/or accumulation, including skin affected by cellulite, when topically applied thereto. In particular, compositions comprising extracts of *Eclipta prostrata* have surprisingly been found to reduce fat accumulation and adipocyte differentiation, as well as increase tenascin-X production, and thus dermal architecture, offering combined mechanisms of action to combating unwanted subcutaneous fat, and in particular cellulite.

In one aspect of the invention, cosmetic compositions are provided for improving the appearance of skin comprising a peroxisome proliferator-activated receptor-gamma (PPARγ) inhibitor in a cosmetically acceptable vehicle in an amount effective to decrease adipocyte differentiation and/or intracellular triglyceride production and/or accumulation in adipocytes in said area of skin, wherein the PPARγ inhibitor further inhibits stearoyl-CoA desaturase1 (SCD1) and/or further stimulates tenascin-X production. In some embodiments, the PPARγ inhibitor is an *Eclipta prostrata* extract, in particular, an ethanol extract of the leaves, stems and flowers of the plant.

In some embodiments, the cosmetic composition further comprises at least one other anti-lipid agent, the anti-lipid agent being selected from the group consisting of a phophodiesterase inhibitor, an adenylate cyclase activator, a lipolysis stimulator, a beta-adrenergic receptor agonist, an alpha-2-adreneric receptor antagonist; a xanthine analog, forskolin, a forskohlii extract, a hawthorne extract, a cola extract, isoproterenol, yohimbine, Ginkgo biloba extract, perilla oil, caffeine, a collagen stimulator, an elastin stimulator, carnitine, creatine and/or a carnitine creatinate salt.

In another aspect, the invention relates to methods for improving the appearance of skin affected by unwanted subcutaneous fat, such as cellulite, comprising topically applying to the skin a cosmetic composition comprising one or more PPARγinhibitors in a cosmetically acceptable vehicle in an amount effective to decrease adipocyte differentiation and/or intracellular triglyceride production and/or accumulation in adipocytes in said area of skin, wherein the PPARγ inhibitor further inhibits stearoyl-CoA desaturase1 (SCD1) and/or further stimulates tenascin-X production. In some embodiments, the PPARγ inhibitor is an *Eclipta prostrata* extract, in particular, an ethanol extract of the leaves, stems and flowers of the plant. For example, an effective amount of the extract of *Eclipta prostrata* in a cosmetically acceptable vehicle can be applied to skin for a time sufficient to improve the appearance of the skin.

In some embodiments, the composition is applied to cellulite found on the thigh, buttocks, abdomen, hip, or upper arm region. In some embodiments, the composition is left on the area of application, e.g., as a leave-on composition. In some embodiments, the composition is applied according to a treatment regimen, such as once a day for a period of at least 4 weeks.

Also provided is a method for reducing the re-occurrence of cellulite in an area previously affected by cellulite, comprising topically applying thereto an effective amount an extract of *Eclipta prostrata* in a cosmetically acceptable vehicle.

Yet another aspect relates to methods for reducing obesity comprising topically applying to an area affected by unwanted fat deposition and/or accumulation an effective amount an extract of *Eclipta prostrata* in a cosmetically acceptable vehicle, for a time sufficient to reduce the unwanted fat.

These and other aspects of the present invention will be better understood by reference to the following detailed description.

DETAILED DESCRIPTION

It has surprisingly been found that compositions comprising one or more substances that inhibit PPARγ, and additionally also inhibit stearoyl-CoA desaturase 1 (SCD1) and/or also stimulate tenascin-X production, markedly improve the appearance of skin affected by unwanted fat deposition and/or accumulation, including skin affected by cellulite, when topically applied thereto. In particular, cosmetic compositions comprising extracts of *Eclipta prostrata* can be used in such methods to improve the appearance of skin affected by cellulite, as well as to reduce the re-occurrence of cellulite in previously-affected area, and/or to reduce obesity in areas affected by unwanted fat accumulation and/or deposition.

In view of these findings and others, a topical composition comprising one or more peroxisome proliferator-activated receptor-gamma (PPARγ) inhibitors is contemplated to be useful in combating cellulite and/or counteracting other signs of unwanted fat deposition and/or accumulation, where the PPARγ inhibitor further inhibits stearoyl-CoA desaturase 1 (SCD1) and/or further stimulates tenascin-X production. It is further contemplated that extracts of *Eclipta prostrate* can find use as active ingredients for such anti-lipid topical compositions, according to the instant disclosure.

PPARγ-Inhibiting Extracts and Compositions

One aspect of the present invention relates to compositions for topical application which comprise one or more PPARγ inhibitors, which also inhibit SCD1 and/or also stimulate tenascin-X production, to treat, ameliorate, inhibit, delay, and/or reduce the signs of excess accumulation and/or production of subcutaneous fat, and/or improve dermal architecture by strengthening connective tissue. Improving the appearance of skin affected by cellulite and/or combating signs of unwanted subcutaneous fat may include without limitation, the following:

(a) reduction in appearance of cellulite lumpiness and/or unevenness;
(b) reduction in pitting appearance of cellulite upon squeezing;
(c) reduction in extent of area affected by cellulite;
(d) prevention or delay in recurrence of cellulite;

(e) reduction in subcutaneous fat deposition and/or accumulation;

(f) improvement in collagen deposition; and (g) improvement in connective tissue strength.

Improvements may be visible, palpable, or perceptible by other means. In practice, the compositions of the invention are applied to skin in need of treatment, that is, skin which suffers from a deficiency or loss in any of the foregoing skin attributes or which would otherwise benefit from improvement in any of the foregoing skin attributes.

A "PPARγ inhibitor" refers to any agent that can decrease the level of triglycerides in human adipocytes via one or more pathways mediated by PPARγ. Decrease in trigyceride levels can refer to a decrease in preadipocyte proliferation and/or adipocyte differentiation and/or intracellular lipid and/or triglyceride production, storage, and/or accumulation in adipocytes, and/or an increase in fatty acid oxidation and/or degradation and/or lipolysis; and/or reduced expression of lipogenic genes, in vitro or in vivo, and can be measured by any means known in the art, or as described herein. For example, the PPARγ inhibitor can act to decrease triglyceride production within human adipocytes. See, e.g., Example 1 below. In some embodiments, triglyceride levels are decreased by at least about 30%, at least about 40%, at least about 50%, at least about 60%, at least about 70%, at least about 75%, or up to about 100%, compared to the level of triglyceride in the absence of the PPARγ inhibitor. As another example, PPARγ inhibition also can be directly measured, e.g., by measuring a reduction in PPARγ gene expression, where the PPARγ inhibitor acts to decrease PPARγ gene expression within human adipocytes. See, e.g., Example 2 below. In some embodiments, PPARγ gene expression is decreased by at least about 10%, at least about 20%, at least about 25%, at least about 30%, at least about 35%, at least about 40%, at least about 50%, or up to about 100%, compared to the level of PPARγ gene expression in the absence of the PPARγ inhibitor.

A PPARγ inhibitor may bring about an effective decrease in triglyceride levels by any means, e.g., by decreasing PPARγ mRNA transcribed and/or decreasing PPARγ protein expressed, and/or decreasing post-translational processing of PPARγ protein in the adipocytes. Other mechanisms of inhibition can include down-regulating an agonist of PPARγ; up-regulating an antagonist of PPARγ; decreasing the stability of PPARγ RNA and/or protein, and/or decreasing dimerization of PPARγ with ligands that effect PPARγ activation. In some embodiments, the PPARγ inhibitor further exhibits one or both of the following properties: (a) inhibiting SCD1; and (b) stimulating tenascin-X. The PPARγ inhibitor can refer to an extract, e.g., an extract of *Eclipta prostrate*, that contains a number of active compounds, one or more of which inhibit PPARγ, while one or more of which may inhibit SCD1 and/or may stimulate tenascin-X.

A "SCD1 inhibitor" refers to any agent that can decrease the level of triglycerides in human adipocytes via one or more pathways mediated by SCD1. Decrease in trigyceride levels can refer to a decrease in adipocyte differentiation and/or intracellular triglyceride production, storage, and/or accumulation in adipocytes, and/or an increase in fatty acid oxidation; and/or reduced expression of lipogenic genes, in vitro or in vivo, and can be measured by any means known in the art, or as described herein. SCD1 inhibition also can be directly measured, e.g., by measuring a reduction in SCD1 gene expression, where the SCD1inhibitor acts to decrease SCD1gene expression within human adipocytes. See, e.g., WO 00/09754 and Example 3 below. In some embodiments, SCD1gene expression is decreased by at least about 40%, at least about 50%, at least about 60%, at least about 70%, at least about 75%, at least about 80%, at least about 85%, at least about 90%, at least about 95%, or up to about 100%, compared to the level of SCD1 gene expression in the absence of the SCD1 inhibitor.

A SCD1 inhibitor may bring about an effective decrease in triglyceride levels by any means, e.g., by decreasing SCD1 mRNA transcribed and/or decreasing SCD1protein expressed, and/or decreasing post-translational processing of SCD1 protein, to decrease the amount of functional enzyme in adipoctyes. Other mechanisms of inhibition can include down-regulating SCD1; up-regulating an antagonist of SCD1; decreasing the stability of SCD1 RNA and/or protein, and/or decreasing SCD1 activity. In some embodiments, the SCD1 inhibitor further exhibits one or both of the following properties: (a) inhibiting PPARγ; and (b) stimulating tenascin-X. The SCD1inhibitor can refer to an extract, e.g., an extract of *Eclipta prostrata*, that contains a number of active compounds, one or more of which inhibit PPARγ, while one or more of which also inhibit SCD1 and one or more of which further may stimulate tenascin-X.

A "tenascin-X stimulator" is an agent that stimulates tenascin-X production to bring about an effective increase in tenascin-X levels by any means, e.g., by increasing tenascin-X mRNA transcribed and/or increasing tenascin-X protein expressed, and/or increasing post-translational processing of tenascin-X protein. Other mechanisms of stimulation can include up-regulating a tenascin-X agonist; down-regulating a tenascin-X antagonist; increasing the stability of tenascin-X RNA and/or protein, and can be measured by any means known in the art, or as described herein. For example, tenascin-X stimulation can be measured by an increase in the activation of the tenascin-X promoter. See, e.g., Example 4 below. In some embodiments, tenascin-X production is increased by at least about 40%, at least about 50%, at least about 60%, at least about 70%, at least about 75%, at least about 80%, at least about 85%, at least about 90%, at least about 95%, at least about 100%, at least about 150%, or at least about 200%, compared to the level of tenascin-X production productin in the absence of the tenascin-X stimulator.

Increase production of tenascin-X may have one or more of the following effects: increasing collagen deposition, improving fibrillar networks, improving dermal architecture, and/or decreasing lipid accumulation in subcutaneous adipose tissue. A tenascin-X stimulator as used herein further exhibits one or both of the following properties: (a) inhibiting PPARγ; and (b) inhibiting SCD1 X. The tenascin-X stimulator can refer to an extract, e.g., an extract of *Eclipta prostrata*, which contains a number of active compounds, one or more of which may inhibit PPARγ, one or more of which also stimulate tenascin-X, and one or more of which further may inhibit SCD1, in some embodiments.

In preferred embodiments, the PPARγ inhibitor is an *Eclipta prostrata* extract. *Eclipta prostrata* is known also as *Eclipta alba, Eclipta erecta, Eclipta punctata, Verbesina alba*, or *Verbesina prostrata*, and by the common names such as "False Daisy", "yerba de tajo", "Bhringaraja", "Kesharaja", "Mahakanni", and "Han Lian Cao." The plant grows natively as an annual herb in wet, warm to temperate regions, including India, China, Philippines, Singapore, Trinidad, and Japan. Its leaves can be cooked and used as a vegetable. It also has traditional medicinal purposes, including as an astringent, emetic, anti-inflammatory, and liver treatment, as well as to delaying graying. (Chevallier, A. *The Encyclopedia of Medicinal Plants* Dorling Kindersley. London 1996; *Medicinal Plants of Nepal*. Dept. of Medicinal Plants, Nepal, 1993). Externally, oil of the plant has been used to treat eczema, dermatitis, psoriasis, herpes zoster, neurodermatitis, and wounds. (See, e.g., CN 101244221 and CN 101385810).

For use in the compositions of this disclosure, the plant, plant components, and/or active ingredients are preferably derived directly from the plant. The components may be in a pure form, a semi-pure form, or unpurified form. In preferred embodiments, the extract of *Eclipta prostrata* comprises an aqueous, alcoholic, or hyrdroalkoholic extract. In more preferred embodiments, components are in the form of an extract obtained by organic solvent extraction, such as using ethanol extraction. See Example 5 below.

Briefly, the organic solvent extraction method involves washing and extracting the plant material using an organic solvent. Non-limiting examples of organic solvents include methanol, ethanol, isopropanol, dichloromethane, chloroform, hexane, xylene, and petroleum ether. Well-known methods in the art may be used for organic solvent extraction.

Organic solvent extraction involves collecting the raw materials from the plant that contain the desired constituent (s), particularly above-ground parts, such as leaves, stems, flowers, bark, and the like. These plant materials are ground to small particle sizes, and then put into an extracting machine through an inlet for the raw materials by a measurable charging machine. The plant raw material is pushed in the extracting machine by a thruster, and slowly moves the plant raw material forward. Organic solvent (e.g., ethanol) may be added into the machine through a solvent inlet at the top of a waste discharge outlet. Due to the difference in gravity and equilibrium, the solvent flows toward the raw material inlet, soaks the materials, and flows out from the opposite side of the solvent inlet. Since the plant materials and the solvent move in opposite directions against each other, the plant materials are constantly immersed in a solution that contains a low-concentration of extract. As a result of equilibrium, high yield of plant constituent(s) may be achieved by continuously extracting the plant material against the low-concentration solution.

An extraction time can be adapted to remove the plant constituents, for example between about 1-8 hours is typical, more preferably being between about 2-6 hours, and most preferably being between about 3-5 hours. The temperature of extraction can be between about 20° C. to about 90° C. (including room temperature extraction), between about 40° C. to about 70° C., or between about 50° C. to about 60° C. The collected extract is then fine-filtered to remove debris, and may be used directly, or may be concentrated, for example by distilling the solvent or by other conventional processing. The extract also can be provided in powder form.

In some embodiments, the extraction comprises aqueous-organic extraction. Generally, aqueous-organic solvent extraction involves initially collecting raw materials from parts of the plant, particularly above-ground parts, such as leaves, stems, flowers, bark, and the like, which are ground into small particle sizes. The ground plant material is soaked in aqueous solution that is acidic or alkaline, depending on the solubility and stability of the desired extract under acidic or alkaline (basic) conditions. For extraction under acidic conditions, an acid such as hydrochloric acid or sulfuric acid is added to water, e.g., at a concentration of about 3% (w/v). For extraction under alkaline conditions, an alkali such as sodium hydroxide or sodium carbonate is added to water. The extraction time and temperature of extraction are typically similar to that used in the organic solvent extraction method described above.

The extract is then collected and fine-filtered to remove debris. Alkaline agents (e.g., ammonia) or acidifying agents (e.g., sulfuric acid) may be added to the extract to neutralize the solution by adjusting the pH, depending on the acidity or alkalinity of the collected extract. The aqueous extract may be used directly, concentrated, or dried. Alternatively, organic solvent may be added to the neutralized solution to transfer the extract actives from an aqueous phase to an organic phase. Examples of such organic solvents include, but are not limited to, ethanol, isopropanol, butanol, pentanol, hexanol and xylene. The extract comprising the transferred extract actives dissolved in organic solvent may be used directly, used as a concentrate, or dried.

Different plants containing different constituents may be mixed and extracted together. This process of mixed extraction preferably is used if extracting two or more plants containing constituents having similar solubility in the solvent used for extraction, such as ethanol. The mixture of extracts may be concentrated and stored in an appropriate solvent.

In some embodiments, the extract is obtained from the leaves, stems, and flowers of the *Eclipta prostrata* plants. In some preferred embodiments, the extracts are obtained by drying the plant material and subsequently extracting from the dried plant using a solvent. For example, a polar solvent may be used. Suitable polar solvents include, but are not limited to, water; alcohols (such as methanol, ethanol, propanol, butanol and the like); glycols; ethers (such as diethyl ether, dipropyl ether, and the like); esters (such as butyl acetate, ethyl acetate, and the like); ketones (such as acetone, ethyl methyl ketone, and the like); organic acids including acetic acid, and the like; dimethyl sulfoxide; acetonitrile; other organic solvents; and combinations thereof. Other suitable solvents include physiological saline, phosphoric acid buffer and phosphate buffer saline and the like. In some preferred embodiments, ethanol is used as the polar solvent.

Preferably, the *Eclipta prostrata* extract is obtained by extracting *Eclipta prostrata* leaves, flowers, and stems with water, ethanol, or a mixture thereof. The solvent systems may comprise from about 10% by volume to about 90% by volume of ethanol, and from about 10% by volume to about 90% by volume of water; from about 25% by volume to about 75% by volume of ethanol and from about 25% by volume to about 75% by volume of water; from about 45% by volume to about 55% by volume of ethanol and from about 45% by volume to about 55% by volume of water; or with a 50:50 mixture (by volume) of ethanol and water.

Additional suitable extraction processes are disclosed in PCT Publications WO03/079816 (describes a process for the preparation of tomato extracts), WO04/014404 (describes a process for the preparation of an *Echinacea angustifolia* extract) and WO04/014958 (describes extracting a polysaccharide of *Echinacea angustifolia* roots), all of which are herein incorporated by reference in their entirety.

In other embodiments, the *Eclipta prostrata* extract, as referred to herein, includes "synthetic" extracts, i.e., where various combinations of known plant components and/or constituents are combined to substantially mimic the composition and/or activity of a plant extract of natural origin. Such synthetic extracts are included in the terms "extract" or "plant extract." The synthetic extracts will have two or more, three or more, or four or more active ingredients in common with a natural plant. Most preferably, the synthetic extracts will have substantially the same number of active ingredients as a natural extract of the plant. The correspondence of the numerical incidence of active ingredients between the synthetic extracts and the plant or a natural plant extract may be described in terms of "percent commonality". Preferably, the synthetic extract has about 50% or more commonality to the chemical composition of a plant or natural plant extract. In other words, the synthetic extract has about 50% or more of the active ingredients found in the plant or a natural plant extract. More preferably, the chemical composition of the synthetic extract has about 70% or more commonality to the chemical composition of a plant or a natural plant extract. Optimally, a synthetic extract has about 90% or more commonality to the chemical composition of a plant or a natural plant extract. The plant or natural plant extract for comparison is derived, for example, from the *Eclipta prostrata* plant, e.g., as described herein.

The *Eclipta prostrata* plant may be in any form including, but not limited to, the whole plant, a dried plant, a ground plant, or parts thereof, including but not limited to, seeds, needles, leaves, roots, bark, cones, stems, rhizomes, callus cells, protoplasts, organs and organ systems, and meristems, an extract, a dried extract, a synthetic extract, or components and/or constituents found in, or isolated from, the plant, and/or portions of the plant, or extracts derived either directly or synthetically from the plant, or any combinations thereof.

Substances found in some extracts *Eclipta prostrata* include ecalbasaponin and coumestan derivatives, such as wedelolactone (7-methoxy-5,11,12-trihydroxycoumestan), demethyl weldelolactone, and desmethyl wedelolacton (see, e.g., EP 595988). Some embodiments may include one or more these substances, while others may be free, or substantially free, of one or more of these substances.

In some embodiments, the PPARγ inhibitor is not used in combination with one or more of the following: Mulberry extract (as in US 2005/0191267); isoflavonoid (as in WO 02/34233 or WO 00/13661 to Avon Products, Inc.); tumeric extracts and/or alpha-hydroxy acids (see, e.g., US 2003/0113388); a phenoxy-pyrrolidine derivative (as in WO 09/019566); a lipoxidase inhibitor (as in KR 776346); dihydroxyacetone (as in U.S. Pat. No. 6,623,725); nor ingested with wine (as in CN 1635075).

Cosmetic compositions of the instant invention generally comprise an amount of a PPARγ inhibitor, e.g., an amount of *Eclipta prostrata* extract, effective to improve the appearance to human skin in an area to which it is topically applied. In preferred embodiments, the compositions comprise an amount of a PPARγ inhibitor effective to decrease adipocyte differentiation and/or intracellular triglyceride production and/or accumulation in adipocytes in the area of skin. In certain preferred embodiments, the cosmetic composition comprises an amount of PPARγ inhibitor from about 0.0001 weight % to about 5 weight % based on the total weight of the composition; preferably from about 0.001 weight % to about 2 weight % based on the total weight of the composition; more preferably from about 0.01 weight % to about 1 weight % based on the total weight of the composition, and even more preferably from about 0.1 weight % to about 0.3 weight %, or about 0.2 weight %, based on the total weight of the composition. The above amounts refer to an "active amount" of the PPARγ inhibitor, such as the amount prostrata extract. The term "active amount" or "dry weight" are used synonymously and refer to the amount of *Eclipta prostrata* extract after solvent and/or other diluents have been removed. Cosmetic compositions described herein find use as anti-lipid agents, e.g., as detailed below.

Cosmetic Use of PPARγ-Inhibiting Compositions

Another aspect of the instant invention relates to cosmetic use of compositions comprising a PPARγ inhibitor, such as an *Eclipta prostrata* extract, where the PPARγ inhibitor further acts to inhibit SCD1 and/or to stimulate tenascin-X production. Such compositions act to ameliorate, inhibit, delay, reduce, and/or improve the signs of excess accumulation and/or production of subcutaneous fat, and/or improve dermal architecture by strengthening connective tissue, and accordingly find use as potent anti-lipid products, and in particular anti-cellulite products.

An "anti-lipid" agent or product, as used herein, refers to any substance that acts to decrease trigyceride levels in adipocytes, such as by bringing about one of more of a decrease in preadipocyte proliferation and/or adipocyte differentiation; a decrease in intracellular lipid and/or triglyceride production, storage, and/or accumulation, an increase in fatty acid oxidation, degradation and/or lipolysis; and/or reduced expression of lipogenic genes, in vitro or in vivo. An "anti-cellulite" agent is product, as used herein, is a substance that exerts in anti-lipid effects so as to produce a visible or palpable improvement in skin affected by cellulite.

In some embodiments, a method is provided for improving the appearance of skin affected by subcutaneous fat production and/or accumulation, such as in the case of cellulite, where the method comprises topically applying to affected skin at least one PPARγ inhibitor in a cosmetically acceptable vehicle, and where the inhibitor also inhibits SCD1 and/or stimulates tenascin-X production. The composition will comprise an effective amount of the substance. An "amount effective" or an "effective amount" to improve appearance to the skin refers to the active amount of a PPARγ inhibitor sufficient to provide a visual improvement in skin affected by unwanted subcutaneous fat when applied to the skin for a sufficient time. Such improvements include without limitation, the following:

(a) reduction in appearance of cellulite lumpiness and/or unevenness;

(b) reduction in pitting appearance of cellulite upon squeezing;

(c) reduction in extent of area affected by cellulite;

(d) prevention or delay in recurrence of cellulite;

(e) reduction in subcutaneous fat deposition and/or accumulation;

(f) improvement in collagen deposition; and (g) improvement in connective tissue strength.

The compositions of the invention can be applied to skin in need of treatment, such as skin which suffers from a deficiency or loss in any of the foregoing attributes or which would otherwise benefit from the composition's anti-lipid effects, e.g., as described herein. For example, the PPARγ inhibitor, such as an Eclipia prostrata extract, can be provided in a cosmetically acceptable vehicle, topically applied to a desired area of skin, and allowed to remain on the area in an amount effective to treat and/or prevent an unwanted feature or condition of the skin, and/or to improve the aesthetic appearance of the skin. Topical application facilitates targeted delivery of the active components, e.g., without the requirement of an injection or the expertise of a health practitioner.

"Treatment" as used herein, as well as related terms such as "treat" or "treating," refers to eradicating, reducing, ameliorating, or reversing one or more of the unwanted features associated with the skin condition being treated, such that the consumer perceives an improvement in the appearance of the skin or other treatment benefit with respect to the condition. "Prevention" as used herein, as well as related terms such as "prevent" or "preventing," refers to affording skin not yet affected by the condition a benefit that serves to avoid, delay, forestall, minimize, or reduce the recurrence/onset of one or more unwanted features associated with the skin condition to be prevented. Such preventative benefits include, for example, delaying development and/or recurrence of the condition, or reducing the duration, severity, or intensity of one or more unwanted features associated with the condition if it eventually develops.

Anti-Cellulite Benefits

Cosmetic compositions taught herein can be applied to an area of skin affected by cellulite to improve the appearance of the skin. An improvement may involve a reduction in appearance of lumpiness and/or unevenness, characteristic of cellulite, preferably reducing what is known as the "cottage cheese" or "orange peel" look. Further, areas of cellulite tend to bulge, pit, and dimple when squeezed or compressed, AS occurs when legs are crossed when seated, which can worsen the appearance of cellulite areas. In some embodiments, an improvement involves a reduction in this pitting appearance of cellulite upon squeezing, so that the look of cellulite on the legs appears reduced even when sitting with the legs crossed. An improvement may also involve reducing the visible depth and/or intensity of cellulite.

Cellulite tends to accumulate on certain body regions, e.g., on the thighs and buttocks of many women, as well as on the abdomen, hip and/or upper arm region. In some embodiments, the extent of the area affected by cellulite is reduced, such that smaller areas of the thigh, buttocks, abdomen, hip, and/or upper arm region remain visibly affected. In preferred embodiments, one of more such regions becomes free of visible signs of cellulite following treatment with a composition described herein. In some particular embodiments, the composition is not applied to skin affected by acne. In some particular embodiments, the composition is not applied to skin of the head and is not used to treat dandruff (as in JP 5-201833; KR 776346; JP 2000143437).

In some embodiments, a method is provided for reducing the re-occurrence of cellulite in an area that was previously affected by cellulite, but showing little or no signs of cellulite currently. Reducing the re-occurrence refers to delaying the recurrence of any cellulite on a previously-affected area, or reducing the extent of cellulite that re-appears on the area, such that any recurrent cellulite is less noticeable than previous amounts.

Compositions for use in the method of the instant invention will comprise a PPARγ inhibitor in an amount sufficient to reduce intracellular triglyceride levels in adipocites at a given area of skin when topically applied thereto. As used herein, reducing trigyceride levels and related expressions refer to a decrease in adipocyte differentiation and/or intracellular triglyceride production, storage, and/or accumulation in adipocytes, and/or an increase in fatty acid oxidation; and/or reduced expression of lipogenic genes, in vitro or in vivo, to decrease the triglyceride content in an area of skin, preferably improving skin appearance to a perceptible extent. For example, in some embodiments, the triglyceride level is decreased by at least about at least about 30%, at least about 40%, at least about 50%, at least about 60%, at least about 70%, at least about 75%, or up to about 100%, compared to the level of triglycerides in the absence of the composition. Triglyceride levels in subcutaneous adipocytes can be determined by appropriate assays, e.g., in vitro assays described herein or known in the art. For example, Example 1 below provides experimental details of assays for measuring intracellular triglyceride levels in human adipocytes.

Without wishing to be bound by theory, compositions disclosed herein act by a number of mechanisms of action to effect improvement in the appearance of skin affected by unwanted subcutaneous fat. The compositions act as PPARγ inhibitors. The peroxisome proliferator-activated receptor gamma (PPAR-gamma) structurally belongs to a superfamily of nuclear transcription factors and activation of this receptor has both physiological and pathological significance, particularly in the control of lipid metabolism and inflammatory response. Nuclear hormone receptors are ligand-dependent intracellular proteins that stimulate transcription of specific genes by binding to specific DNA sequences following activation by the appropriate ligand. PPARγ activity is governed by binding small lipophilic ligands, mainly fatty acids, derived from nutrition or metabolic pathways that also are often controlled by PPARγ. Indeed, PPARγ is purported to be the centerpiece of a feed-forward pathway that favors differentiation and energy storage by adipocytes. The PPARγ inhibitor may act to inhibit any of these pathways, and can break up fatty deposits, even in mature fat cells.

The compositions may act also as SCD1 inhibitors. A key enzyme involved in regulating membrane lipids is the membrane-bound stearoyl-CoA desaturase 1 (SCD1), which is the rate-limiting enzyme in the cellular synthesis of mono-unsaturated fatty acids from saturated fatty acids. A proper ratio of saturated to mono-unsaturated fatty acids contributes to membrane fluidity. Oleic acid and palmitoleic acid are the major monounsaturated fatty acids in fat depots and membrane phospholipids and these fatty acids are synthesized by SCD1. The PPARγ inhibitor may also act as a SCD1inhibitor, action at any of these pathways.

Thus, without wishing to be bound by theory, compositions disclosed herein act to combat signs of cellulite via more than one mechanism of action. That is, PPARγ inhibitors used in the methods provided also either inhibit SCD1 and/or stimulate tenascin-X production. PPARγ-inhibiting and SCD1-inhibiting activities work to decrease subcutaneous fat deposition and/or accumulation and/or decrease adipocyte differentiation, as described above. PPARγ and SCD1 are adipocyte differentiation markers, and their combined inhibition represents combined action to reduce adipocyte differentiation. Tenascin-X, on the other hand, improves dermal architecture, e.g., by increasing collagen deposition, and thereby strengthening the dermis and connective tissue. A stronger dermal structure reduces the likelihood of fat nodules "blebbing" between connective tissue fibers or septa, which is believed to lead to the characteristic unsightly appearance of cellulite. Further, lower levels of subcutaneous fat further reduce the likelihood of such blebbing. As cellulite is believed to result from a combination of enlarged fat tissue and weak dermal structure, combating cellulite through these multiple approaches, as described herein, can provide superior results compared with products that utilize only one approach.

Accordingly, the invention provides novel mechanisms of action to improve the appearance of cellulite, and thus potent ant-cellulite compositions for use therein.

In some embodiments, the cosmetic compositions for combating signs of unwanted subcutaneous fat can further comprise additional anti-lipid agents. For example, the cosmetic composition comprising PPARγ inhibitors in an amount effective (or amounts effective) to improve the appearance of skin may further comprise at least one other anti-lipid agent, including one other anti-cellulite agent. It is contemplated that synergistic improvements may be obtained with such combinations, in some embodiments.

Exemplary anti-cellulite agents include, without limitation, phosphodiesterase inhibitors, such as xanthine analogs (e.g. caffeine and aminophylline, theophylline); adenylate cyclase activators, such as forskolin and Coleus forskohlii extract; lipolysis stimulators, such as hawthorne extract and cola extract; beta adrenergic receptor agonists, such as isoproterenol; alpha-2-adrenergic antagonists, such as yohimbine and Ginkgo biloba extract; perilla oil (see, e.g., U.S. Pat. No. 7,410,658); carnitine, creatine, and/or carnitine creatinate salts (see, e.g., US 2007/0264205 entitled "Cosmetic Composition having Carnitine Creatinate and Methods for Using", incorporated herein by reference in its entirety). In some embodiments, additional actives may include a collagen stimulator and/or an elastin stimulator, e.g., a substance that stimulates elastin production, and/or a glycosaminoglycan enhancer. Examples of collagen, elastin and glycosaminoglycan enhancers include, e.g., fennel extract, carrot extract, and alfalfa extract. In some embodiments, the additional actives may include a collagenase inhibitor and/or elastase inhibitor. In some embodiments, the invention relates to synergistic action of one or more compositions described herein with perilla oil, e.g., to provide enhanced anti-cellulite benefits to skin.

Anti-Obesity Benefits.

In some embodiments, a method is provided for reducing obesity. The method can comprise topically applying to an area affected by unwanted fat deposition an effective amount of a PPARγ inhibitor, such as an *Eclipta prostrata* extract, in a cosmetically acceptable vehicle, for a time sufficient to reduce the unwanted fat. The PPARγ inhibiting, and optionally the SCD1 inhibiting, activities of the composition can reduce fat accumulation and/or adipocyte differentiation, as described herein, to reduce weight, preferably in targeted areas. Such areas may be "problem areas" from which the consumer finds it difficult to loose weight by general dieting and/or exercise. Other approaches for regulating SCD1 to treat obesity have been described and may be used with the PPARγ inhibitors, e.g., the *Eclipta prostrata* extract, disclosed herein. See, e.g., WO 04/047746.

Other Benefits

In some other embodiments, it is contemplated that compositions described herein, such as cosmetic compositions comprising an *Eclipta prostrata* extract, will exhibit one or more benefits on aesthetic appearance, selected from the following:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in skin texture and/or promotion of re-texturization;
(h) improvement in skin barrier repair and/or function;
(i) treatment and/or prevention of skin sagging or atrophy; and/or
(j) improvement in appearance of skin contours;
(k) restoration of skin luster and/or brightness;
(l) replenishment of essential nutrients and/or constituents in the skin;
(m) improvement of skin appearance decreased by menopause;
(n) improvement in skin moisturization and/or hydration; and
(o) improvement of skin elasticity and/or resiliency.

Based on the teachings provided herein, one of skill in the art will recognize other cosmetic and/or pharmaceutical applications for the compositions described herein, and such applications are also contemplated as within the scope of the instant invention. For example, compositions described herein may also find use in personal care products, such as skin care products, where it is desirable to produce an improvement in the appearance of skin, as described herein, upon application of the product. Personal care products for the skin include, for example, body lotions, body tonics, and the like. It is contemplated, for example, that compositions described herein can find use in lotion and/or tonic formulations that decrease the appearance of cellulite and other unwanted subcutaneous fat on various surfaces of the body.

Treatment Regimens

The invention provides methods for improving the appearance of skin by topically applying a composition comprising a PPARγ inhibitor over an area of skin for a period of time sufficient to improve the appearance of skin, as described herein. The composition will typically be applied to the skin in accordance with a treatment regime. The treatment regiment can comprise application one, two, or three times daily for as long as is necessary to achieve desired results, such as the anti-cellulite benefits described herein. This treatment regiment may comprise daily application or every-other-day application for at least about one week, at least about two weeks, at least about three weeks, at least about four weeks, at least about six weeks, at least about eight weeks, at least about twelve weeks, or more. See, e.g., Example 6 below. In some embodiments, the composition is applied more than once daily for the recited periods of time, for example, twice daily, preferably once in the morning and once again at night before bed. The composition preferably is massaged thoroughly onto the area to be treated, e.g., onto the thighs, buttocks, hips, abdomen, upper arms, and the like.

Chronic treatment regimens are also contemplated, e.g., with respect to prophylactic treatments aimed at forestalling one or more signs of skin cellulite or other unwanted subcutaneous fat; as well as with respect to reducing and/or preventing the recurrence of cellulite in an area previously affected thereby. The treatment and/or prophylactic regime may also depend on concentration of the PPARγ inhibitor being used, e.g., as different concentrations may produce anti-cellulite skin benefits more quickly than others.

The compositions generally are topically applied to the skin for a period of time sufficient to improve the appearance of skin affected by cellulite or other unwanted subcutaneous fat. In some embodiments, the compositions are left on the skin as a "leave-on" composition, by which is meant they are applied in a formulation that is allowed to remain in the skin without being deliberately washed and/or rubbed off for a certain period of time. For example, the composition may be left on the skin for a day, overnight, or for at least about 18 hours, for at least about 12 hours, for at least about 8 hours, or for at least about 4 hours. In some particular embodiments, the compositions are not soaps or other bath products, which are washed off shortly after application, e.g., as described in KR 2004083994, JP 2009013128, and JP 2000143437.

PPARγ inhibitors, such as *Eclipta prostrata* extracts, may be used to formulate cosmetic compositions, as known in the art. The cosmetic compositions find use in anti-cellulite and anti-lipid products, preferably formulated for topical application to the skin e.g., with a cosmetically acceptable vehicle. Formulations for cosmetic products comprising PPARγ inhibitors, including *Eclipta prostrata* extracts, are described in more detail below.

Formulations of *Eclipta prostrata* Extracts and other PPARγ Inhibitors

In accordance with the invention, the PPARγ inhibitors, including *Eclipta prostrata* plant extracts, may be formulated in a variety of product forms. The compositions may be prepared in targeted delivery systems, e.g. creams, lotions, gels, toners, serums, transdermal patches, and the like, particularly for topical administration. For example, the invention encompasses compositions comprising a cosmetically or dermatologically acceptable formulation which is suitable for contact with living animal tissue, particularly human tissue, with virtually no or little adverse physiological effect to the user. Compositions embraced by this invention can be provided in any cosmetically and/or dermatologically suitable form, preferably as a lotion or cream, but also in an anhydrous or aqueous base, as well as in a sprayable liquid form. Other suitable cosmetic product forms for the compositions include, for example, an emulsion, a cream, a balm, a gloss, a lotion, a mask, a serum, a toner, an ointment, a mousse, a patch, a pomade, a solution, a spray, a wax-based stick, or a towelette.

In some particular embodiments, the cosmetic composition comprising a PPARγ inhibitor, such as an *Eclipta prostrata* extract, is provided in the form a cream for topical application to skin affected, previously-affected, or likely-to-be affected by cellulite. In some particularly preferred embodiments, the cream comprising the PPARγ inhibitor is supplied along with a gel for use with the cream, for example, by following application of the cream with application of the gel to the same area of skin. The gel preferably provides tightening polymers to enhance the cellulite-reducing effects of the cream. In more preferred embodiments, the gel provides a cooling sensation to the skin when applied to the skin following and/or upon application of the cream. Exemplary composition of a cream and gel as described herein are provided in Example 7 below. The cream and gel may be provided in different containers, or in different compartments of the same container. In some embodiments, the cream and gel are provided in a "tube-within-a-tube" that dispenses the cream and gel together. This allows the cream and gel to be mixed upon dispensing, e.g., immediately before application to the skin.

In addition, the compositions contemplated may include one or more compatible cosmetically acceptable adjuvants commonly used and known by the skilled practitioner, such as colorants, fragrances, emollients, humectants, preservatives, vitamins, chelators, thickeners, perilla oil or perilla seed oil (WO 01/66067 to a "Method of Treating a Skin Condition," incorporated herewith) and the like, as well as other botanicals such as aloe, chamomile, and the like, and as further described below.

Also embraced by the invention are transdermal modes of delivery, such as patches and the like, with or without suitable penetration enhancers. The methods and compositions embodied by the invention provide a means by which the PPARγ inhibitor, such as an *Eclipta prostrata* extract, can be effectively administered in a transdermal system or device. Examples of such devices are known in the art, e.g., as disclosed in U.S. Pat. Nos. 5,146,846; 5,223,262; 4,820,724; 4,379,454; and 4,956,171, all of which are incorporated herein by reference and such descriptions are not meant to be limiting. In a preferred method, topical application is through a sustained release vehicle, carrier, or diluent, e.g., using a topically applied sustained released patch. Preferably, when a topical patch is used, the patch is applied to the desired area for extended period of time, such as, e.g., at least about 4 hours, at least about 8 hours, at least about 12 hours, at least about 16 hours, or at least about 24 hours. In some embodiments, the extended period of time is all day, e.g., from the morning to bedtime, or overnight, e.g., while the user is sleeping.

The PPARγ inhibitors, such as *Eclipta prostrata* extracts, of the present invention are preferably contained in a cosmetically or dematologically acceptable vehicle, medium, diluent or carrier, give a topical formulation for use in treating, ameliorating, preventing, inhibiting, delaying, and/or reducing the signs of excess accumulation and/or production of subcutaneous fat, and/or improving dermal architecture, including improving the appearance of skin affected by cellulite.

In some embodiments, the topical formulation comprises a medium (vehicle, diluent or carrier) that is compatible with human skin. The compositions can be formulated as an aqueous phase, an oil phase, alcohol, or aqueous/alcohol-based solutions, ointments, lotions, gels, wax-in-water emulsions, or water-in-oil, oil-in-water, of water-oil-water emulsions, e.g., having the appearance of creams, gels, microemulsions, or aerosols.

The aqueous phase is a mixture of one or more water soluble or water dispersible substances, which can be liquid, semi-solid or solid at room temperature (25° C.). The vehicle comprises or can be in the form of a suspension, dispersion, or solution in water or an aqueous-alcoholic vehicle, which may contain a thickener or gellant. A person skilled in the art can select the appropriate cosmetic form, the ingredients contained therein, as well as the method for preparing it, on the basis of the knowledge that the skilled artisan possesses.

In some embodiments, the composition may include an aqueous phase which may contain water or a mixture of water and at least one hydrophilic organic solvent, in particular an alcohol, especially a linear or branched lower monoalcohol containing from 2 to 5 carbon atoms, e.g., ethanol or propanol; a polyol, e.g., propylene glycol, sorbitol, glycerol, diglycerol, panthenol, or polyethylene glycol, and mixtures thereof. This aqueous phase may represent from about 0.5 weight % to about 99.99 weight %, based upon the total weight of the composition.

In some embodiments, when the composition of the invention is in the form of an emulsion, the composition may also optionally comprise a surfactant, preferably in an amount from about 0.1 weight % to about 30 weight %, and in particular, from about 1 weight % to about 20 weight %, based upon the total weight of the composition.

In some embodiments, the composition may also comprise a thickening polymer such as an amphiphilic polyurethane, a polyacrylic homopolymer or copolymer, a polyester, and/or a hydrocarbon-based resin.

The invention also contemplates formulations that may comprise an oil phase containing oil-soluble or oil-dispersible substances, which are liquid at room temperature (25° C.) and/or oily or waxy substances that are solid at room temperature, such as waxes, semi-solids, gums, and mixtures thereof. The waxes can include hydrocarbon-based waxes, fluoro waxes and/or silicone waxes and can be of plant, mineral, animal and/or synthetic origin. Formulations typically comprise from about 0 weight % to about 20 weight % waxes, based upon total weight. The gums used are generally high molecular weight PDMSs, cellulose gums or polysaccharides, and the semi-solid materials are generally hydrocarbon-based compounds, such as, but not limited to, lanolins and derivatives thereof. This oily phase may also contain organic solvents.

Suitable oily materials that are liquid at room temperature, often referred to as oils, include hydrocarbon-based oils of animal origin such as perhydrosqualene; hydrocarbon-based plant oils such as liquid triglycerides of fatty acids of 4 to 10 carbon atoms, for instance, heptanoic or octanoic acid triglycerides, or oils such as sunflower oil, corn oil, soybean oil, grapeseed oil, castor oil, avocado oil, caprylic/capric acid triglycerides, jojoba oil; linear or branched hydrocarbons of mineral or synthetic origin, such as liquid paraffins and derivatives thereof, petroleum jelly; synthetic esters and ethers, in particular esters of fatty alcohols, namely; for example, isopropyl myristate, 2-ethylhexyl palmitate, 2-octyldodecyl stearate, isostearyl isostearate; hydroxylated esters such as isostearyl lactate, octyl hydroxystearate, octyldodecyl hydroxystearate, heptanoates, octanoates and decanoates of fatty alcohols; polyol esters such as propylene glycol dioctanoate, neopentyl glycol diheptanoate, diethylene glycol diisononanoate, and pentaerythritol esters; fatty alcohols containing from 12 to 26 carbon atoms such as octyldodecanol, 2-butyloctanol, 2-hexyldecanol, 2-undecylpentadecanol, oleyl alcohol; partially hydrocarbon-based fluoro oils and/or fluorosilicone oils; silicone oils such as volatile or non-volatile, linear or cyclic polydimethylsiloxanes (PDMS) that are liquid or semisolid at room temperature such as cyclomethicones and dimethicones, optionally comprising a phenyl group, for instance phenyl trimethicones, siloxanes, and mixtures thereof. These oils are usually present in an amount of about 0 weight % to about 90 weight %, preferably from about 1 weight % to about 80 weight % by weight of the oil phase.

The oil phase of the formulation may also comprise one or more cosmetically acceptable organic solvents. These solvents are present in an amount of from about 0 weight % to about 60 weight %, preferably from about 1 weight % to about 30 weight %, based on the total weight of the composition, and may be selected from the group consisting of lipophilic organic solvents, amphiphilic organic solvents, and mixtures thereof. Suitable solvents which may be used in the composition of the invention include acetic acid esters such as methyl, ethyl, butyl, amyl or 2-methoxyethyl acetate; isopropyl acetate; hydrocarbons such as toluene, xylene, p-xylene, hexane or heptane; ethers containing at least 3 carbon atoms, and mixtures thereof. In some other embodiments, the compositions can be in the form of vesicular dispersions containing ionic and/or nonionic lipids, as described above.

In yet other embodiments, the compositions are formulated into liposomes or microspheres, which can comprise other additives or substances, and/or which can be modified to more specifically target or remain at a site following administration. (See, e.g., U.S. Pat. No. 5,770,222 to Unger et al., incorporated herein by reference).

The formulations for use in the inventive methods may further comprise any ingredient conventionally used in the cosmetics field. These ingredients include, e.g., preserving agents, aqueous phase thickeners (polysaccharide biopolymers, synthetic polymers) fatty-phase thickeners, fragrances, hydrophilic and lipophilic active agents, and mixtures thereof. The amounts of these various ingredients are those conventionally used in the cosmetics field to achieve their intended purpose, and range typically from about 0.01 weight % to about 20 weight %, based upon the total weight of the composition or formulation. The nature of these ingredients and their amounts will be selected to be compatible with the production and intended applications of the compositions, as described herein.

In some embodiments, the formulation may comprise a particulate phase, typically present in an amount of from about 0 weight % to about 30 weight %, based upon the total weight of the composition or formulation, preferably from about 0.05 weight % to about 20 weight %, and which can comprise pigments and/or pearlescent agents and/or fillers used in cosmetic compositions.

Suitable inorganic pigments include, but are not limited to, titanium oxide, zirconium oxide and cerium oxide, as well as zinc oxide, iron oxide, chromium oxide and ferric blue. Suitable organic pigments include barium, strontium, calcium, and aluminium lakes and carbon black. Suitable pearlescent agents include mica coated with titanium oxide, with iron oxide, or with natural pigment. Fillers are normally present in an amount from about 0 weight % to about 20 weight %, based on the total weight of the composition or formulation, preferably from about 0.1 weight % to about 10 weight %. Suitable fillers include talc, silica, zinc stearate, mica, kaolin, nylon (in particular orgasol) powder, polyethylene powder, Teflon, starch, boron nitride, copolymer microspheres such as Expancel (Nobel Industrie), Polytrap (Dow Coming), and silicone resin microbeads (Tospearl from Toshiba).

In some particular embodiments, the compositions for topical application can be in the form of a person care product for the skin, preferably for the thighs, buttocks, legs, hips, abdomen, limbs, upper arms, or other areas of the body. Non-limiting examples include creams or lotions, salves, ointments, gels, masks, artificial tanning compositions, patches, or a solid which is poured or cast as a stick or a dish, for example.

In some embodiments, the topical formulations may also include one or antioxidants. An antioxidant functions, among other things, to scavenge free radicals from skin, protecting the skin from environmental aggressors. Examples of antioxidants that may be used in the present compositions and formulations include compounds having phenolic hydroxy functions, such as ascorbic acid and its derivatives/esters; thiodipropionic acid and its esters; vitamins A, C, or E; polyphenols, beta-carotene; catechins; curcumin; ferulic acid derivatives (e.g. ethyl ferulate, sodium ferulate); gallic acid derivatives (e.g. propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may have an antioxidant preferably from about 0.001 weight % to about 10 weight %, and more preferably from about 0.01 weight % to about 5 weight %, based on the total weight of the composition or formulation.

In some embodiments, the topical formulations may also include one or more of the following: a skin penetration enhancer, an emollient, a skin plumper, an exfoliation promoter, and an optical diffuser. Details with respect to these and other suitable cosmetic ingredients can be found in the International Cosmetic Ingredient Dictionary and Handbook, 10th Edition (2004), published by the Cosmetic, Toiletry, and Fragrance Association (CTFA), at pp. 2177-2299, which is herein incorporated by reference in its entirety.

An emollient provides the functional benefits of enhancing skin smoothness and may aid in improving the appearance of skin affected by cellulite and other unwanted subcutaneous fat. Examples of emollients include isopropyl myristate, petrolatum, isopropyl lanolate, silicones (e.g., methicone, dimethicone), oils, mineral oils, fatty acid esters, or any mixtures thereof. The emollient is preferably present from about 0.1 wt % to about 50 wt% of the total weight of the composition or formulation.

A skin plumper serves as a collagen enhancer to the skin. An example of a suitable, and preferred, skin plumper is palmitoyl oligopeptide. Other skin plumpers are collagen and/or glycosaminoglycan (GAG) enhancing agents. The skin plumper is preferably present from about 0.1 weight % to about 20 weight % of the total weight of the composition or formulation.

In some embodiments, formulations may have one or more exfoliation promoters. Suitable examples of exfoliation promoters include alpha hydroxy acids (AHA); benzoyl peroxide; beta hydroxy acids; keto acids, such as pyruvic acid, 2-oxopropanoic acid, 2-oxobutanoic acid, and 2-oxopentanoic acid; oxa acids as disclosed in U.S. Pat. Nos. 5,847,003 and 5,834,513 (the disclosures of which are incorporated herein by reference); salicylic acid; urea; or any mixtures thereof. The preferred exfoliation promoters are 3,6,9-trioxaundecanedioic acid, glycolic acid, lactic acid, or any mixtures thereof. When an embodiment of the invention includes an exfoliation promoter, the formulation may have from about 0.1 weight % to about 30 weight %, preferably from about 1 weight % to about 15 weight %, and more preferably from about 1 weight % to about 10 weight %, of the exfoliation promoter based on the total weight of the composition or formulation.

An optical diffuser is a particle that changes the surface optometrics of skin, resulting in a visual blurring and softening of, for example, lines and wrinkles, as well as lumpiness and unevenness caused by cellulite and other unwanted subcutaneous fat. Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, or any mixtures thereof. The optical diffuser is preferably present from about 0.01 weight % to about 20 weight %, based on the total weight of the composition or formulation.

In some embodiments, formulations may have one or more retinoids. Exemplary retinoids include, without limitation, retinoic acid (e.g., all-trans or 13-cis) and derivatives thereof, retinol (Vitamin A) and esters thereof, such as retinol palmitate, retinol acetate and retinol propionate, and salts thereof.

In some embodiments, formulations may have one or more sunscreen protectors. A sunscreen protects the skin from damaging ultraviolet rays. In an illustrative embodiment of the invention, the sunscreen would provide both UVA and UVB protection, by using either a single sunscreen or a combination of sunscreens. Among the sunscreens that can be employed in the present compositions or formulations are avobenzone, cinnamic acid derivatives (such as octylmethoxy cinnamate), octyl salicylate, oxybenzone, titanium dioxide, zinc oxide, or any mixtures thereof. The sunscreen may be present in an amount from about 1 weight % to about 30 weight % of the total weight of the composition or formulation. The compositions or formulations of the invention having sunscreen bring about additional improvements to the aesthetic appearance of skin, including at least one of the following: minimizing sun-burning and/or reducing redness.

In some embodiments, the formulation may also have one or more of the following cosmetic and pharmaceutical active agents, excipients, ingredients, or adjuvants: anesthetics, antibiotics, e.g., erythromycins and tetracyclines, salicylic acids, anti-allergenics, anti fungals, antiseptics, anti-irritants, anti-inflammatory agents, antimicrobials, analgesics, nitric oxide synthase inhibitors, insect repellents, self-tanning agents, skin penetration enhancers, skin cooling agents, chelating agents, colorants including dyes, lakes and pigments that may be untreated or chemically surface treated to improve wetability or some other property, demulcents, emulsifiers, fragrances, humectants, lubricants, skin protectants, moisturizers, pH adjusters, preservatives, stabilizers, surfactants, thickeners, film formers, plasticizers, viscosity modifiers, vitamins, blood flow stimulators, or any mixtures thereof. The amounts of these various substances are those that are conventionally used in the cosmetic or pharmaceutical fields to achieve their intended purposes, for example, they may constitute from about 0.01 weight % to about 20 weight % of the total weight of the composition or formulation.

Emulsifiers are typically present in the compositions or formulations of the invention in an amount from about 0.01 weight % to about 30 weight %, and preferably from about 0.5 weight % to about 30 weight %, based on the total weight of the composition or formulation. In some other embodiments, the composition or formulation is free or substantially free of emulsifiers.

Non-limiting examples of suitable thickening agents include xanthan gum, hydroxypropyl cellulose, hydroxyethyl cellulose, carbomer, gum acacia, Sepigel 305 (available from Seppic Co., France), and clays such as magnesium aluminum silicate.

The topical compositions of the present invention may include, and their utility can be enhanced, by one or more humectants, such as ureas, pyrrolidone carboxylic acids, amino acids, sodium hyaluronates, certain polyols and other compounds with hygroscopic properties.

The general activity and mildness to skin of the present topical compositions can also be enhanced by neutralization to a pH from about 3.5 to about 7.0, most preferably a pH from about 3.7 to about 5.6. This neutralization is preferably accomplished with one or more of ammonium hydroxide, potassium hydroxide, sodium hydroxide, arginine or other amino acids, and/or triethanolamine.

All terms used herein are intended to have their ordinary meaning unless otherwise provided. As used herein, "% by weight" or "% wt" refers to the weight percent of a component in relation to the total weight of the composition or formulation (i.e., including any carriers, vehicles, solvents, emollients, fillers, or other components added before application to the skin) unless otherwise specified.

EXAMPLES

Example 1

Reduction of Intracellular Triglycerides by *Eclipta prosata*

Cryopreserved human primary pre-adipocytes harvested from the subcutaneous adipose tissue of a healthy female, with a normal BMI of 21.67, were obtained from Zen-Bio (Research Triangle Park, N.C.). Following the manufacture's instructions, the pre-adipocytes were cultured in Pre-adipocyte medium containing DMEM/Ham's F-12 (1:1, v/v), HEPES (pH 7.4), fetal bovine serum, penicillin, streptomycin, and amphotericin B (Zen-Bio), in a humidified 37° C. incubator with 5% $CO_2$. After reaching 90% confluence, the pre-adipocytes were allowed to differentiate into adipocytes by adding Adipocyte Differentiation medium containing DMEM/Ham's F -12 (1:1, v/v), HEPES pH 7.4, fetal bovine serum, biotin pantothenate, human insulin, dexamethasone, isobutylmethylxanthine, PPAR agonist, penicillin, streptomycin, amphotericin B (Zen-Bio).

To treat adipocytes with *Eclipta protrata* extract, the extract was dissolved in adipocytes differentiation medium and added into cell culture for 7 days and 14days. The untreated adipocytes were used as a control. The production of triglyceride in adipocytes was determined by using a triglyceride assay kit (Zen-Bio). Briefly, adipocytes were rinsed with a wash buffer and lysed in a lysis buffer following medium removal. Intracellular triglycerides were released into the lysis buffer and converted into glycerol-1-phosphate, which was subsequently oxidized to di-hydroxyacetone phosphate and hydrogen peroxide. Hydrogen peroxide was reacted with 4-aminoantipyrine (4-AAP) and sodium N-ethyl-N-(3-sulfopropyl)m-anisidine (ESPA) to generate a quinoeimine dye, which shows an absorbance maximum at 540 nm. The increase in absorbance at 540 nm is directly proportional to the intracellular levels of triglycerides in the adipocytes. Results are presented below in Table 1.

TABLE 1

| Concentration of Eclipta prostrata Extract Solution (Equivalent concentration of Dry Eclipta prostrata Extract) | % change | p value |
|---|---|---|
| 0.08% (0.03%) | −61.58 | 0.00 |
| 0.15% (0.056%) | −73.54 | 0.00 |

Human adipocytes treated with the indicated weight % of Eclipia prostrata extract showed a significant % decrease in intracellular triglyceride levels, as indicated in Table 1.

Example 2

Reduction of PPAR-gamma Gene Expression by Eclipta prosata

Human adipocytes were allowed to differentiate from pre-adipocytes and were then treated with Eclipta prostrata extract for 7 days, as described in Example 1. At the end of treatment, RNA was extracted from the adipocytes using RNA Easy mini kit (Qiagen, Calif.). RNA was quantified on the Nanodrop ND-1000 Spectrophotometer (NanoDrop Technologies) and RNA with a 260/280 ratio of 2.1 was further processed for cDNA preparation. Reverse transcription was carried out on 2 μg RNA using the SuperScript first strand synthesis system (Cat No: 12371-019, Invitrogen, Calif.) according to the manufacturer's instructions.

PPARγ RNA abundance was measured using quantitative Real-Time PCR with 18S rRNA as the internal control. Gene expression was performed by using human specific TaqMan primers for the PPARγ gene (Applied Biosystems cat. number HS01115513_ml) and 18S gene (Applied Biosystems cat. number HS99999901_sl). PCR was performed on an Applied Biosystems ABI Prism 7300 Real Time PCR system (Perkin-Elmer Applied Biosystems Inc.) under the following conditions: 50° C. (2 min) for 1 cycle, 95° C. (10 min) for 1 cycle, 95° C. (15 s), 60° C. (1 min) for 40 cycles. All samples were run in triplicate and normalized to the 18S, and results were expressed as a percentage of the control, as presented in Table 2.

TABLE 2

| Concentration of Eclipta prostrata Extract (Equivalent concentration of Dry Eclipta prostrata Extract) | % change | p value |
|---|---|---|
| 0.15% (0.056%) | −30.22 | 0.02 |

Human adipocytes treated with the indicated weight % of Eclipta prostrate extract showed a significant % decrease in PPARγ gene expression, as indicated in Table 2.

Example 3

Reduction of SCD1 Gene Expression by Eclipta prosata

Human adipocytes were allowed to differentiate from pre-adipocytes and were then treated with Eclipta prostrata extract for 7 days, as described in Example 1. RNA isolation and cDNA preparation were conducted as described in Example 2. RNA abundance of SCD1 was measured using quantitative Real-Time PCR and 18S rRNA was used as an internal control. Gene expression was performed using human specific TaqMan primers for SCD1 gene (Applied Biosystems cat. number Hs01682761_ml) and 18S gene (Applied Biosystems cat. number HS99999901_s1).

PCR was performed on an Applied Biosystems ABI Prism 7300 Real Time PCR system (Perkin-Elmer Applied Biosystems Inc.) under the following conditions: 50° C. (2 min) for 1 cycle, 95° C. (10 min) for 1 cycle, 95° C. (15 s), 60 ° C. (1 min) for 40 cycles. All samples were run in triplicate and normalized to 18S, and results were expressed as a percentage of the control, as presented in Table 3.

TABLE 3

| Concentration of Eclipta prostrata Extract (Equivalent concentration of Dry Eclipta prostrata Extract) | % change | p value |
|---|---|---|
| 0.15% (0.056%) | −85.99 | 0.001 |

Human adipocytes treated with the indicated weight % of Eclipta prostrate extract showed a significant % decrease in SCD1 gene expression, as indicated in Table 3.

Example 4

Activation of Tenascin-X Promoter by Eclipta prosata

A human tenascin-X promoter reporter gene was constructed by inserting a DNA fragment containing ~5.0 kb upstream promoter sequence of the human tenascin-X gene into the pGL3 luciferase reporter (Promega, Wis.). A tenascin-X promoter DNA fragment was generated by PCR amplification of human DNA. The promoter region of tenascin-X was confirmed by DNA sequencing. The tenascin-X promoter reporter DNA was transfected into HT1080-fibrosarcoma cells by using LipofectAMINE and Plus Reagent (Invitrogen, Calif.). Following the vendor's instructions, a transfection mixture was generated by mixing tenascin-X promoter reporter DNA, plasmid pRL-NULL, Plus reagen and DMEM. The transfection complexes were added to HT1080 cells at 85% confluence. After a 3 hr-incubation, the media was replaced by normal culture medium and incubated overnight in a 37° C. humidified incubator with 5.0% CO$_2$.

After 24h-transfection, the transfected cells were treated with &lipla prostrata extract diluted to various concentrations with water. The treated cells were cultured for additional 24 hours, washed once with phosphate buffered saline, and lysed in cell lysis buffer. Cell lysates were collected for determination of luciferase activity. The treatment was conducted in triplicate and water was used vehicle control. Luciferase activity was determined with a Dual-Luciferase Reporter Assay System (Promega, Wis.) as described by the manufacturer. Briefly, an aliquot of lysate was mixed with Luciferase Assay Reagent II and the intensity of firefly luminescence was recorded by luminometer. Subsequently, the firefly luminescence was quenched and the Renilla luminescence was simultaneously activated by adding Stop & Glo Reagent to the sample. The firefly luminescence signal was directly proportion to the luciferase activity, after being normalized by the Renilla luminescence signal.

The percentage change of luciferase activity of Eclipta-treated cells over that of vehicle-treated cells was determined, as presented in Table 4 below.

TABLE 4

| Concentration of *Eclipta prostrata* Extract (Equivalent concentration of Dry *Eclipta prostrata* Extract) | % change | p value |
|---|---|---|
| 0.02% (0.0075%) | +86 | <0.05 |

Human adipocytes treated with the indicated weight % of *Eclipta prostrata* extract showed a significant % increase in human tenascin-X promoter activation, as indicated in Table 4.

Example 5

*Eclipta prostrata* Extraction Procedure

*Eclipta prostrata* can be extracted from natural raw materials by using methods of aqueous-organic solvent extraction as is well known in the art, e.g., as set forth below.

An extract can be obtained by extracting the leaves, flowers, and stems of the *Eclipta prostrata* plant using an ethanol extraction scheme. Briefly, leaves, flowers, and stems of *Eclipta prostrata* can be first manually ground into small particles resulting in a powder of about 250 grams per flask (2 flasks). The ground powder can be then extracted with 80% ethanol (2×2,000 ml per flask). Alternatively, the homogenized plant material can be combined with an equivalent volume of ethanol, shaken in a sealed container for 30-120 minutes at 200 rpm, and centrifuged for 10 min at 4000×g, in order to form a clear ethanol layer in the upper phase. After filtering and vacuum evaporation, the total concentrated extract can be lyophilized to give an ethanolic extract of *Eclipta prostrata*.

Example 6

Consumer Study

A consumer study indicated that use of a cosmetic cream comprising an *Eclipta prostrata* extract reduced the appearance of cellulite after a 4 week treatment.

Example 7

Exemplary Compositions

The cosmetic composition of a cream comprising an extract of *Eclipta prostrata* (equivalent dry weight=0.075%) for topical application to the skin is provided in Table 5 below, along with the cosmetic composition of a gel with which it can be used for optimal results.

TABLE 5

| Ingredient | wt % of Cream | wt % of Gel |
|---|---|---|
| Demineralized Water | QS | QS |
| Polymeric Thickener | 0.4 | 0.6 |
| Gelling agent | — | 0.4 |
| Solvent | 5.0 | 23.0 |
| Emulsifier | — | 2.0 |
| Humectant | 6.0 | 0.5 |
| Menthol | — | 0.2 |
| Gelling Agent/Emulsifier Blend | 2.0 | — |
| Caffeine | 0.2 | 0.2 |
| Carrot Root (*Daucus Carota Sat.*) Extract | 1.0 | 0.1 |
| Chelating agent | 0.2 | 0.05 |
| pH Adjusting agent | 0.4 | 0.55 |
| Film forming polymer | — | 1.0 |
| Polyethylene Glycol Stearate Blend | 1.25 | — |
| Emollient | 0.6 | — |
| Preservative | 1.0 | — |
| Silicone Emulsifier | 0.35 | — |
| Oils and Waxes | 11.85 | — |
| Cola Extract-Powder | 1.0 | — |
| Hawthorne (*Crataegus Monogyna*) Fruit Extract | 1.0 | — |
| Milk Thistle (*Silybum Marianum*) Extract | 1.0 | — |
| Bitter Orange (*Citrus Aurantium Amar.*) Extract | 1.0 | — |
| Alfalfa (*Medicago Sat.*) Extract | 1.0 | — |
| Fennel (*Foeniculum Vulg.*) Fruit Extract | 1.0 | — |
| *Eclipta Prostrata* Extract | 0.20 | — |
| Colorant | 1.27 | — |
| Fragrance | 0.5 | — |

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for improving the appearance of skin affected by cellulite comprising topically applying thereto an effective amount of an extract of *Eclipta prostrata* in a cosmetically acceptable vehicle for a time sufficient to improve the appearance of said skin.

2. The method according to claim 1, wherein said *Eclipta prostrata* extract is in combination with at least one other anti-lipid agent.

3. The method according to claim 2, wherein said at least one other anti-lipid agent comprises at least one agent selected from the group consisting of a phophodiesterase inhibitor, an adenylate cyclase activator, a lipolysis stimulator, a beta-adrenergic receptor agonist, and an alpha-2-adreneric receptor antagonist.

4. The method according to claim 2, wherein said at least one other anti-lipid agent comprises at least one agent selected from the group consisting of a xanthine analog, forskolin, a forskohlii extract, a hawthorne extract, a cola extract, isoproterenol, yohimbine, *Ginkgo biloba* extract, and perilla oil.

5. The method according to claim 2, wherein said at least one other anti-lipid agent is caffeine.

6. The method according to claim 1, wherein said *Eclipta prostrata* extract is in combination with at least one collagen and/or elastin stimulator.

7. The method according to claim 1, wherein said *Eclipta prostrata* extract is in combination with carnitine, creatine, and/or a carnitine creatinate salt.

8. The method according to claim 1, wherein said cellulite is found on a thigh, buttocks, abdomen, hip, and/or upper arm region.

9. The method according to claim 1, wherein said composition is a leave-on composition.

10. The method according to claim 1, wherein said topical application comprises daily application for a period of at least 4 weeks.

11. A method for improving the appearance of skin affected by cellulite comprising topically applying thereto a composition comprising a peroxisome proliferator-activated receptor-gamma (PPARγ) inhibitor in a cosmetically acceptable vehicle in an amount effective to decrease adipocyte differentiation and/or intracellular triglyceride production and/or accumulation in adipocytes in said area of skin, for a time sufficient to improve the appearance of said skin; wherein said PPARγ inhibitor is an *Eclipta prostrate* extract, and
    wherein said PPARγ inhibitor further inhibits stearoyl-CoA desaturasel (SCD1) and/or further stimulates tenascin-X production.

12. The method according to claim 11, wherein said PPARγ inhibitor is in combination with at least one other anti-lipid agent.

13. The method according to claim 12, wherein said at least one other anti-lipid agent comprises at least one agent selected from the group consisting of a phophodiesterase inhibitor, an adenylate cyclase activator, a lipolysis stimulator, a beta-adrenergic receptor agonist, and an alpha-2-adreneric receptor antagonist.

14. The method according to claim 12, wherein said at least one other anti-lipid agent comprises at least one agent selected from the group consisting of a xanthine analog, forskolin, a forskohlii extract, a hawthorne extract, a cola extract, isoproterenol, yohimbine, *Ginkgo biloba* extract, and perilla oil.

15. The method according to claim 12, wherein said at least one other anti-lipid agent is caffeine.

16. The method according to claim 11, wherein said cellulite is found on a thigh, buttocks, abdomen, hip, and/or upper arm region.

17. The method according to claim 11, wherein said composition is a leave-on composition.

18. The method according to claim 11, wherein said topical application comprises daily application for a period of at least 4 weeks.

19. A method for reducing the re-occurrence of cellulite in an area previously affected by cellulite comprising topically applying thereto an effective amount an extract of *Eclipta prostrata* in a cosmetically acceptable vehicle.

20. A method for reducing obesity comprising topically applying to an area affected by unwanted fat deposition and/or accumulation an effective amount an extract of *Eclipta prostrata* in a cosmetically acceptable vehicle, for a time sufficient to reduce said unwanted fat.

21. A method according to claim 1, further comprising allowing said extract to mix with a gel before and/or upon said topical application, wherein said gel comprises an agent for imparting a cooling sensation to the skin.

* * * * *